US012761225B2

(12) United States Patent
Pigeot-Rémy et al.

(10) Patent No.: US 12,761,225 B2
(45) Date of Patent: Oct. 13, 2026

(54) DEVICE FOR COLLECTING, PRESERVING AND STORING EUKARYOTIC CELLS CONTAINED IN A SAMPLE OF BIOLOGICAL FLUID FOR FURTHER CELL ANALYSIS

(71) Applicant: Ahlstrom Oyj, Helsinki (FI)

(72) Inventors: Stéphanie Pigeot-Rémy, Sainte Colombe (FR); Marie-Laure Boen, Belleregarde-Poussieu (FR); Noël Cartier, Jardin (FR); Christophe Béesau, Montreuil (FR); Vincent Petit, Paris (FR)

(73) Assignee: Ahlstrom Oyj, Espoo (FI)

( * ) Notice: Subject to any disclaimer, the term of this patent is extended or adjusted under 35 U.S.C. 154(b) by 1272 days.

(21) Appl. No.: 17/427,690

(22) PCT Filed: Feb. 3, 2020

(86) PCT No.: PCT/FI2020/050064

§ 371 (c)(1),
(2) Date: Aug. 2, 2021

(87) PCT Pub. No.: WO2020/157388

PCT Pub. Date: Aug. 6, 2020

(65) Prior Publication Data

US 2022/0349900 A1 Nov. 3, 2022

(30) Foreign Application Priority Data

Feb. 1, 2019 (FR) ...................................... 1901018

(51) Int. Cl.

*G01N 33/68* (2006.01)
*B01L 3/00* (2006.01)
*G01N 33/575* (2026.01)

(52) U.S. Cl.

CPC ........ *G01N 33/6872* (2013.01); *B01L 3/5055* (2013.01); *G01N 33/5759* (2026.01);
(Continued)

(58) Field of Classification Search

None
See application file for complete search history.

(56) References Cited

U.S. PATENT DOCUMENTS 6,271,046 B1 * 8/2001 Chandler ......... G01N 33/54388 436/514
2005/0252820 A1 * 11/2005 Sanchez-Felix ... A61B 10/0045 206/569

(Continued)

FOREIGN PATENT DOCUMENTS

AU 2014201346 A1 * 4/2014 ......... A61B 10/0045
WO WO2012145379 A1 10/2012

(Continued)

OTHER PUBLICATIONS

P. Rous, J R Turner, The Preservation of Living Red Blood Cells in Vitro : I. Methods of Preservation (Abstract), J Exp Med. Feb. 1, 1916;23(2):219-37. doi: 10.1084/jem.23.2.219. (Year: 1916).*

*Primary Examiner* — Lyle Alexander
*Assistant Examiner* — Mickey Huang
(74) *Attorney, Agent, or Firm* — Laine IP Oy

(57) ABSTRACT

A device for collecting, preserving and storing a sample of biological fluid comprising a porous medium for collecting and maintaining the membrane integrity of the eukaryotic cells contained in the sample, and their constituents is disclosed, the medium comprising at least 80% by weight of artificial components, advantageously at least 85%, preferably at least 90% of a total weight of the medium; and having a mean flow pore size (MFP) of at least 3 μm.

18 Claims, 6 Drawing Sheets

(52) U.S. Cl.
CPC . *B01L 2300/0816* (2013.01); *B01L 2300/123* (2013.01); *B01L 2400/0406* (2013.01)

(56) References Cited

U.S. PATENT DOCUMENTS

| | | | | |
|---|---|---|---|---|
| 2012/0095369 | A1* | 4/2012 | Teixeira | A61M 1/77 600/573 |
| 2014/0018701 | A1* | 1/2014 | Mao | H01J 49/0436 600/583 |
| 2014/0137792 | A1 | 5/2014 | Ward et al. | |
| 2016/0103046 | A1* | 4/2016 | Ivosevic | A61B 5/150022 422/549 |

FOREIGN PATENT DOCUMENTS

| | | | |
|---|---|---|---|
| WO | WO2016156376 | A1 | 10/2016 |
| WO | WO2017180909 | A1 | 10/2017 |

* cited by examiner

| | PRESENCE OF A CELLULAR PELLET | | | | | | | | | | | | | | | | | | | | | |
|---|---|---|---|---|---|---|---|---|---|---|---|---|---|---|---|---|---|---|---|---|---|---|
| | 24 hours | | | | 72 hours | | | | | | | | | | | | | | | | | |
| | Wet medium | | Dry medium | | Wet medium | | Composition (in % by total weight of the medium) | | | | | | | | | | | | | | | |
| | 4 °C | Room temperature | 4 °C | Room temperature | 4 °C | Room temperature | Glass fibers | Micro glass fibers | PVOH fibers | PV OH | Cotton | Viscose | PET | Lyocell® | Polysorbate 20 | BSA | Acrylic styrene latex | Weight (g/m²) | Thickness (µm) at 100 Kpa | Air permeability 200 Pa (l/m².s) | MFP (µm) |
| Medium No. 1 | Yes | Yes | Yes | Yes | Yes | Yes | 0% | 0% | 0% | 0% | 0% | 0% | 100% | 0% | 0% | 0% | 0% | 110 | 1100 | 1800 | 70 |
| Medium No. 2 | Yes | Yes | Yes | Yes | Yes | Yes | 91% | 0% | 0% | 9% | 0% | 0% | 0% | 0% | 0% | 0% | 0% | 74 | 324 | 2772 | 119 |
| Medium No. 3 | Yes | Yes | Yes | Yes | Yes | Yes | 91% | 0% | 0% | 9% | 0% | 0% | 0% | 0% | 0% | 0% | 0% | 78 | 335 | 1635 | 66 |
| Medium No. 4 | Yes | Yes | Yes | Yes | Yes | Yes | 91.5% | 0% | 0% | 9% | 0% | 0% | 0% | 0% | 0% | 0% | 0% | 42 | 233 | 4283 | 68 |
| Medium No. 5 | Yes | Yes | Yes | Yes | Yes | Yes | 99% | 0% | 0% | 0% | 0% | 0% | 0% | 0% | 0.2% | 0% | 0% | 74 | 324 | 2773 | 119 |
| Medium No. 6 | Yes | Yes | Yes | Yes | Yes | Yes | 0% | 0% | 0% | 0% | 0% | 0% | 90% | 0% | 0% | 0% | 10% | 75 | 342 | 1413 | 47 |
| Medium No. 7 | Yes | Yes | Yes | Yes | Yes | Yes | 88% | 0% | 0% | 12% | 0% | 0% | 0% | 0% | 0% | 0% | 0% | 75 | 380 | 2700 | 34 |
| Medium No. 8 | Yes | Yes | Yes | Yes | Yes | Yes | 0% | 0% | 0% | 0% | 0% | 0% | 99.5% | 0% | 0.2% | 0% | 0% | 100 | 370 | 1778 | 76 |
| Medium No. 9 | Yes | Yes | Yes | Yes | Yes | Yes | 80% | 0% | 0% | 0% | 0% | 0% | 0% | 0% | 0% | 0.4% | 0% | 74 | 324 | 2772 | 119 |
| Medium No. 10 | Yes | Yes | Yes | Yes | Yes | Yes | 83% | 0% | 13% | 0% | 0% | 0% | 0% | 4% | 1% | 0% | 0% | 80 | 432 | 2205 | 126 |
| Medium No. 11 | Yes | Yes | Yes | Yes | Yes | Yes | 30% | 0% | 3% | 0% | 0% | 57% | 10% | 0% | 0% | 0% | 0% | 114 | 509 | 2400 | 111 |
| Medium No. 12 | Yes | Yes | Yes | No | - | - | 7% | 80% | 0% | 3% | 0% | 0% | 0% | 0% | 0% | 0% | 0% | 57 | 283 | 205 | 12 |
| Medium No. 13 | Yes | Yes | No | No | - | - | 0% | 0% | 0% | 0% | 100% | 0% | 0% | 0% | 0% | 0% | 0% | 179 | 480 | 30 | 12 |
| Medium No. 14 | Yes | Yes | No | No | - | - | 0% | 0% | 0% | 0% | 100% | 0% | 0% | 0% | 0% | 0% | 0% | 289 | 825 | 40 | 14 |
| Medium No. 15 | No | No | No | No | No | No | 100% | 0% | 0% | 0% | 0% | 0% | 0% | 0% | 0% | 0% | 0% | 67 | 324 | 19.5 | 2.2 |
| Medium No. 16 | No | No | No | No | No | No | 100% | 0% | 0% | 0% | 0% | 0% | 0% | 0% | 0% | 0% | 0% | 280 | 1112 | 19.4 | 2.9 |

Fig. 8

DEVICE FOR COLLECTING, PRESERVING AND STORING EUKARYOTIC CELLS CONTAINED IN A SAMPLE OF BIOLOGICAL FLUID FOR FURTHER CELL ANALYSIS

FIELD

The invention refers to the field of the analysis of cells contained in a sample of biological fluid using a medium able to maintain the membrane integrity of the cells.

In the description that follows and in the claims, the expression "biological fluid" denotes a whole blood sample (that is to say comprising plasma, red blood cells, white blood cells, and platelets), urine, saliva, pus, serous fluid, vaginal fluid, tears, or feces.

More specifically, aspects of the invention relate to a device for collecting, preserving and storing a biological sample, within which the membrane integrity of both cells and their constituents is preserved, with a view to subsequent analyses, such as cell phenotype, quantification of biomarkers, assay of cellular and enzymatic functions, isolation of intracellular organelles, etc.

The cells concerned are mainly red blood cells and/or white blood cells and/or cancer cells, as far as blood samples are concerned. They are essentially white blood cells and/or cancer cells and/or any cell which can be isolated with regard to the other samples, namely a sample of urine, saliva, pus, serous fluid, vaginal fluid, tears, or feces. They are therefore eukaryotic cells.

By way of example, other cell types can be isolated from urine or saliva sample, such as epithelial cells or even parasites such as protist species.

A "cancer cell" refers to a normal cell whose genome has accumulated several alterations. The cancer cell becomes minimally sensitive or insensitive to the mechanisms of tissue homeostasis (mechanisms of DNA control and repair, apoptosis, etc.) and has an indefinite capacity for proliferation (immortalization).

It should be noted that red blood cells are eukaryotic cells despite the absence of a nucleus. Indeed, during the differentiation of the proerythroblast into erythrocytes (or red blood cells), hemoglobin accumulates in the cytoplasm which leads to the condensing of the nucleus, which is then expelled from the cell.

The collection of the eukaryotic cells mentioned above also makes it possible to subsequently have access to numerous components of cells, such as organelles, proteins, nucleic acids, intracellular parasites, etc.

BACKGROUND

The analysis of the biological fluid cells is currently carried out on samples collected by means of a standard sample. As regards, for example, blood, it is a sample of several milliliters collected by means of a venipuncture or arterial puncture device (needle and sampling body or butterfly needle), the content of which is stored in collection tubes. For other types of biological samples, they can be stored directly in sterile boxes.

There are other techniques for collecting a biological sample, but which do not make it possible to maintain the membrane integrity of the cells and therefore do not allow cell analysis.

In particular, mention may be made of the technology known as "Dried Blood Spot" (DBS). It consists in collecting a blood sample on a fibrous support (historically cotton), called blotting paper or filter paper, to dry it, store it at room temperature then use it later for analyses of the molecules and/or biomolecules present in the blood. Conventionally used fibrous supports are cotton bases. At room temperature, the cells dry, which leads to their drying and their lysis. The cells thus lose their membrane integrity making the sample unsuitable for cell analysis. In practice, the analysis of dried blood drops makes it possible to carry out assays of proteins, metabolites or deoxyribonucleic acid (DNA), in particular with a view to diagnosing cancers, metabolic diseases such as phenylketonuria, or genetic diseases such as sickle cell anemia or cystic fibrosis.

The collection of a biological fluid sample on a fibrous support has also been implemented within the framework of the development of the technology known as "Lateral Flow Assays" (LFA). This technology is based on paper-based devices intended to detect the presence or absence of a target compound (proteins, metabolites, etc.) in liquid samples, without requiring specialized and expensive equipment. According to this technology, the sample is deposited on a first fiber-based medium, called a collection medium. In this medium, the sample is treated by retaining certain constituents by filtration, which could alter the analysis so that said sample is compatible with the test. The sample then migrates laterally by capillary action, towards a second fiber-based medium, called a "conjugated medium." The role of this medium is to accept the conjugate, to keep it stable throughout the storage period, and to release it in an efficient and reproducible manner. In practice, the medium is treated with particles on which are grafted antibodies or antigens on the basis of the target sought. When the sample passes through the conjugated medium, the target molecule to be analyzed binds to the conjugate and the complex thus formed, then passes over a nitrocellulose membrane, within which the presence of the target molecule is detected. Generally, the test is chromatographic, that is to say that the result of the analysis is visual. In practice, a colored band indicates that the test has worked (control band) and another band colors if it is positive.

By way of example, if the analysis aims to identify the presence of an antigen such as the β subunit of the gonadotropic chorionic hormone or β-hCG, the conjugate will be an antibody directed specifically against this antigen, i.e. an anti-β-hCG antibody.

More specifically, the anti-β-hCG conjugation antibody is labeled for example with a colored particle (e.g. purple latex particle). The antibody captures the (β-hCG contained in the urine. By capillary action, the formed antigen/antibody complex (β-hCG/anti-β-hCG antibody—colored latex particle), as well as the anti-hCG-colored latex antibody alone, migrate laterally by capillary action. The formed antigen/antibody complex encounters the anti-β-hCG capture antibody at the test zone to form a complex (anti-β-hCG capture antibody/β-hCG/anti-β-hCG conjugation antibody/colored latex particle). It is the formation of this complex which allows the coloring of the test strip. The conjugation anti-β-hCG antibody, not coupled with β-hCG, continues its migration to the control band where it encounters the anti-β-hCG antibody, which in turn attaches it on the control band. A colored band is formed at the window, a check making it possible to validate that the test has worked well, in particular in the case where it is negative.

These technologies make it possible to conduct qualitative and quantitative analyses, such as the identification and determination of molecules, for example, essentially proteins, intra and/or extracellular metabolites, or DNA. Indeed, the use of cellulose (DBS) or nitrocellulose (LFA) induces drying of the cells present in the sample to be tested. This results in a loss of the integrity of the cell membranes (plasma and nuclear membranes), which makes any cell analysis, such as, for example, the identification of cell populations, impossible.

One problem which the invention addresses is therefore that of developing a collection device which can be used directly by the user, along the lines of "LFA" and "DBS," and which makes it possible to preserve the membrane integrity of cells in a biological sample for subsequent cell analysis.

More specifically, one problem which the invention addresses is therefore that of developing a collection, conservation and storage medium which can maintain the membrane integrity of eukaryotic cells for a time sufficient to allow for biological analyses and tests which are otherwise impossible to carry out with available technologies, namely DBS and LFA.

DETAILED DESCRIPTION

The Applicant has found that, quite surprisingly, the use of a medium based on artificial components alone, or in combination with a binding agent, makes it possible to respond to the problems mentioned above.

More specifically, in one aspect, there is disclosed a device for collecting, preserving and storing a sample of a biological fluid comprising a porous medium for collecting and maintaining the membrane integrity of the eukaryotic cells contained in the sample, and of their constituents, the medium comprising at least 80% by weight of artificial components, advantageously at least 85%, preferably at least 90%; and having a mean flow pore size (MFP) of at least 3 μm.

In the description that follows and in the claims, the acronym MFP designates the "Mean Flow Pore size," measured according to ASTM F316-03 (2011) standard.

For the purposes of the disclosure, "eukaryotic cells" are cells having a nucleus and internal compartments delineated by membranes. These are red blood cells (or erythrocytes), white blood cells (leukocytes), and cancer cells.

For the remainder of the disclosure, the terms "eukaryotic cells" and "cells" are used interchangeably.

For the purposes of the disclosure, "preservation of membrane integrity" is used to indicate that the plasma membrane of the cell is not damaged or destroyed. In other words, the eukaryotic cell has an external physical appearance compatible with cellular or subcellular analyses, without having undergone membrane lysis, whether the eukaryotic cell is alive, in quiescence, or dead after collection. It does not matter that all of the cells in the biological fluid sample have retained their membrane integrity. Indeed, it suffices that a sufficient quantity of cells has retained their membrane integrity to have a representative sample and be able to carry out the desired analysis. Many technologies allowing to study cells individually can be used on this type of biological sample.

Advantageously, the device according to aspects of the invention allows the membrane integrity of eukaryotic cells and their constituents to be preserved. For example, the integrity of plasma, nuclear, mitochondrial, or even lysosomal membranes is preserved.

For the purposes of the disclosure, "sufficient quantity of cells" is at least one eukaryotic cell which has preserved the integrity of its plasma membrane.

According to an aspect of the invention, the cells collected are individualized.

According to the disclosure, the term "storage" means maintaining the integrity of the cell membranes at temperatures that are adapted on the basis of the nature of the biological sample, as per the knowledge of a person skilled in the art. For example, storage can occur at room temperature (23-25° C.) or 4° C.

Advantageously, the devices described herein allow for storage of the biological sample at a room temperature (23-25° C.) while preserving the membrane integrity of the cells. For example, the storage of a blood sample can occur at room temperature.

According to a particular embodiment, the artificial component is chosen from the group comprising artificial fibers, advantageously semi-synthetic fibers and/or synthetic fibers, and artificial foams.

For the purposes of the disclosure, "artificial" means manufactured or produced by man, that is to say not existing in the natural state.

For the remainder of the disclosure, the terms "artificial component" and "artificial material" are used interchangeably.

For the purposes of the disclosure, "semi-synthetic fibers" are fibers for which materials of natural origin have been transformed and/or regenerated after passing through a spinneret to form fibers. By way of example, these are rayon, Lyocell®, diacetate, triacetate, or even modal fibers.

For the purposes of the disclosure, "synthetic fibers" are fibers for which the basic chemical units have been obtained by chemical synthesis followed by the formation of fibers. By way of example, these are fibers based on polymers such as polyethylene terephthalate (PET), polybutylene terephthalate (PBT), polypropylene (PP), polyethylene (PE), nylon, polyvinyl chloride (PVC), aramid, polyurethane (PU), or even elastomer fibers, glass fibers and glass microfibers.

According to a particular embodiment, the medium is a nonwoven material.

The devices described herein may have the advantage of use of a minimally invasive collection which can be collected directly by the user, that is to say a patient or a healthcare staff member. The volume of the sample taken is small, advantageously between 10 μL and 50 μL and therefore creating less inconvenience for the individual providing the collection. These two characteristics offer a definite advantage over a standard blood test for a cell analysis which requires a collection of a minimum 4 mL for an adult.

A further advantage is the preservation of the membrane integrity of eukaryotic cells for a time sufficient to allow their analysis. The delay can be several hours, even several days. Those skilled in the art know how to verify that the membrane integrity of eukaryotic cells has been preserved by performing an analysis after elution of the cells from the medium.

By way of example, the determination of the preservation of the integrity of the plasma membrane can be verified by analysis with a phase contrast microscope, by immunological labeling, for example of membrane proteins, or even by labeling using intercalating agents of the nucleic acids making it possible to characterize a membrane permeability and therefore a loss of integrity, for example propidium iodide (PI) or 4',6-diamidino-2-phenylindole (DAPI). Indeed, membrane permeabilization allows the entry of all types of compounds independently of the physiological mechanisms of active or passive transport.

For information purposes, PI is a cationic dye and an intercalating agent of nucleic acids without basic specificity which allows it to react with DNA or RNA. This compound is excited at 488 nm, and emits fluorescence at 617 nm when it is linked to DNA.

Its use, especially in flow cytometry, is linked to its relatively high lipophobicity, which prevents it from easily crossing plasma membranes, except damaged ones. Said characteristic makes this compound a powerful marker of the integrity of the plasma membrane and therefore of cell viability. In the case of a viable cell, PI cannot penetrate and bind to the DNA of the cell, unlike a dead cell which has a permeabilized, weakened membrane.

Another technique, more specifically specific to blood or whole blood, consists in centrifugation of the sample. If a sufficient quantity of eukaryotic cells has retained its membrane integrity, a pellet is formed at the bottom of the tube after centrifugation due to the different density gradient between plasma and light cellular debris. Thus, the plasma and light cellular debris are located in the supernatant, whereas the heavier intact cells are stored in the pellet.

On the other hand, in the case where too many cells have lost their membrane integrity, there will be no density gradient allowing the constituents of the sample to be separated. Consequently, the sample after centrifugation will be in the form of a homogeneous liquid, that is to say, without separation of pellet/supernatant.

In other words, the presence of a cell pellet characterizes the preservation of the membrane integrity of the cells. Conversely, the absence of pellet characterizes the absence of membrane integrity of the cells. Thus, one skilled in the art can know without particular effort whether the membrane integrity of the cells, after elution from the medium, has, at least in part, been preserved.

One skilled in the art would further know how to choose a method of determining membrane integrity on the basis of the type of sample collected.

Thus, the membrane integrity of the cells contained in a blood sample can be determined either by the method of centrifugation and identification of the presence of a cell pellet, or, by an analysis under a phase contrast microscope, or by immunological labeling, or by labeling with a DNA intercalating agent.

The membrane integrity of the cells contained in other samples, namely a sample of urine, saliva, pus, serous fluid, vaginal fluid, tears or even feces, can be determined either by phase contrast microscopic analysis, by immunological labeling, or by labeling with a DNA intercalating agent.

Advantageously, the medium participates in, allows and/or ensures the collection and preservation of membrane integrity.

The physical properties of the medium according to the invention, in terms of mechanical strength, weight and absorbent capacity depend on several factors, among which the quantity, type and nature of the artificial components included in the medium according to the invention, preferably semi-synthetic fibers and/or synthetic fibers. The preservation of the membrane integrity of the cells contained in the sample of biological fluid is obtained thanks to the nature and the quantity of the fibers of the medium, preferably a nonwoven material.

Thus, in one aspect, the medium of the device contains at least 80% by weight of artificial components, advantageously at least 85%, preferably at least 90%, and even more preferably at least 95% of a total weight of the medium.

According to a specific embodiment, semi-synthetic fibers are selected from the group comprising: rayon fibers, Lyocell® fibers, viscose fibers, and mixtures thereof.

According to a particular embodiment, the synthetic fibers are chosen from the group comprising: polyethylene terephthalate (PET) fibers, glass fibers, glass microfibers, and their mixtures.

According to a particular embodiment, the medium contains exclusively artificial components, preferably semi-synthetic and/or synthetic fibers, and is advantageously devoid of binding agents.

According to a particular embodiment, the MFP of the medium is at least 3 μm, at least 4 μm, at least 5 μm, or even at least 10 μm, advantageously between 10 μm and 200 μm, preferably between 30 μm and 180 μm, preferentially between 45 μm and 150 μm. The MFP parameter is a critical point to ensure the preservation of the integrity of the cells stored by the device. Indeed, if the MFP of the medium is below 3 μm, the integrity of the membrane of the cells cannot be ensured.

As already said, the parameter corresponding to the mean flow pore size or MFP is measured according to standard ASTM F316-03 (2011). The measurement can be carried out by any means known to those skilled in the art, in particular a porometer. It may, for example, be a porometer of advanced permeability PMI (or PMI Advanced Perm Porometer).

According to a particular embodiment, the thickness of the medium according to the invention is between 100 and 2500 μm, preferably between 200 and 1200 μm.

According to the invention, the thickness of the medium is measured by the TAPPI/ANSI T411 om-15 (2015) method, identical to the ASTM D645/D645M-97 (2007) standard. The only difference with this measurement method corresponds to the application of a pressure per surface of 100 KPa, instead of 50 KPa. This alternative to the parameter of pressure applied is presented by the thickness measurement method as being acceptable.

According to the invention, "air permeability" is the air flow through the 2 surfaces of a material under a known air pressure differential. This parameter is measured by the ASTM D737-18 (2018) standard by means of a prescribed air pressure differential of 200 Pa.

According to a particular embodiment, the air permeability of the medium is between 10 and 5000 $L/m^2 \cdot s$, preferably between 25 and 4500 $L/m^2 \cdot s$. Applicant had found that a porosity greater than 5000 $L/m^2 \cdot s$ decreases the recovery level of white blood cells.

According to a particular embodiment, the artificial component, preferably semi-synthetic fibers and/or synthetic fibers, has a moisture regain value of less than approximately 5%.

According to the invention, the "moisture regain value" is measured by the ASTM D629-15 (2015) standard.

According to another particular embodiment, the artificial component, preferably the semi-synthetic fibers and/or the synthetic fibers, has a contact angle with water of less than approximately 75°, advantageously less than approximately 60°.

According to the invention, the "contact angle with water" is measured by the ASTM D7490-13 (2013) standard.

Advantageously, the artificial component according to the invention, preferably semi-synthetic fibers and/or synthetic fibers, has a diameter of at least 3 μm.

According to another particular embodiment, the medium consists of PET fiber for 100% of its mass, the MFP advantageously being between 50 μm and 100 μm, preferably between 65 μm and 75 μm, the thickness being advantageously included between 800 μm and 1500 μm, preferably between 1050 μm and 1150 μm.

However, the cohesion of the fibers can be improved by adding a binder, which can, if necessary, itself be in the form of fibers. Advantageously, the medium, preferably the nonwoven, can contain up to 15% by weight of a binder, advantageously up to 10%.

According to a particular embodiment, the binder is chosen from the group comprising polyvinyl alcohol (PVOH) and the latexes, preferably the latexes of acrylic styrenes.

A particularly advantageous binder for the medium of this invention is PVOH.

Advantageously, the PVOH is in the form of fibers.

According to a particular embodiment, the binder is chosen from the group comprising polyvinyl alcohol (PVOH), advantageously in the form of fibers, and the latexes, preferably the latexes of acrylic styrenes.

According to a particular embodiment, the medium according to the invention consists of a mixture of glass fibers and/or PET fibers in combination with PVOH.

According to another particular embodiment, the medium consists of glass fibers in combination with PVOH, the MFP advantageously being between 50 μm and 150 μm, preferably between 60 μm and 125 μm, the thickness being advantageously included between 200 μm and 400 μm, preferably between 300 μm and 350 μm.

According to a particular embodiment, the medium consists of glass fibers in combination with PVOH in the form of fibers, the MFP being advantageously between 40 μm and 100 μm, preferably between 60 μm and 70 μm, the thickness advantageously being between 200 μm and 500 μm, preferably between 300 μm and 350 μm.

According to a particular embodiment, the medium consists of glass fibers in combination with PVOH, the MFP being advantageously between 50 μm and 200 μm, preferably between 90 μm and 130 μm, the thickness being advantageously between 150 μm and 400 μm, preferably between 200 μm and 250 μm.

According to a particular embodiment, the medium consists of glass fibers in combination with PVOH and a surface active agent (or surfactant), for example, polysorbate 20, the MFP being advantageously between 50 μm and 300 μm, preferably between 90 μm and 150 μm, the thickness being advantageously between 200 μm and 450 μm, preferably between 300 μm and 350 μm.

According to a particular embodiment, the medium consists of PET fibers in combination with an acrylic binder, for example, an acrylic styrene latex, the MFP being advantageously between 20 μm and 80 μm, preferably between 40 μm and 50 μm, the thickness being advantageously between 200 μm and 500 μm, preferably between 300 μm and 400 μm.

According to a particular embodiment, the medium consists of glass fibers in combination with PVOH, the MFP being advantageously between 50 μm and 150 μm, preferably between 75 μm and 100 μm, the thickness being advantageously between 400 μm and 700 μm, preferably between 550 μm and 600 μm.

According to a particular embodiment, the medium consists of glass fibers in combination with PVOH in the form of fibers, viscose fibers and PET fibers, the MFP being advantageously between 50 μm and 200 μm, preferably between 100 μm and 130 μm, the thickness being advantageously between 400 μm and 700 μm, preferably between 450 μm and 550 μm.

According to a particular embodiment, the medium consists of glass fibers and glass microfibers in combination with PVOH, the MFP being advantageously between 5 μm and 50 μm, preferably between 8 μm and 15 μm, the thickness advantageously being between 200 μm and 500 μm, preferably between 250 μm and 300 μm.

According to a particular embodiment, the medium consists of PET fibers in combination with a tension active agent (or surfactant), for example, polysorbate 20, the MFP advantageously being between 50 μm and 150 μm, preferably between 65 μm and 85 μm, the thickness being advantageously between 200 μm and 500 μm, preferably between 350 μm and 400 μm.

According to a particular embodiment, the medium consists of glass fibers in combination with PVOH and proteins, for example, bovine serum albumin (or BSA), the MFP being advantageously between 80 μm and 200 μm, preferably between 100 μm and 140 μm, the thickness being advantageously between 200 μm and 400 μm, preferably between 300 μm and 350 μm.

According to a particular embodiment, the medium consists of glass fibers in combination with the PVOH in the form of fibers, a tension active agent (or surfactant), for example polysorbate 20, and Lyocell®, the MFP advantageously being between 80 μm and 200 μm, preferably between 115 μm and 130 μm, the thickness being advantageously between 300 μm and 500 μm, preferably between 400 μm and 450 μm.

In order to be able to preserve the membrane integrity of eukaryotic cells, the medium must make it possible to maintain the sample in an environment allowing the liquid part, and/or possibly the serum, of the biological fluid to be preserved.

To do this, the medium, preferably a nonwoven material, advantageously has an MFP of at least 3 μm, advantageously between 10 μm and 200 μm, preferably between 30 μm and 180 μm preferentially between 45 μm and 150 μm.

According to a particular embodiment, the medium according to the invention has a thickness of between 100 μm and 2500 μm advantageously between 200 μm and 1200 μm.

According to a particular embodiment, to improve the shelf life of eukaryotic cells, the medium according to the invention is impregnated with an isotonic preservative (or isotonic preservation buffer), such as, conventionally, phosphate buffered saline (PBS), possibly combined with one or more anticoagulant agents (ethylenediaminetetraacetic acid (EDTA), heparin, citrate dextrose (ACD) etc.) and/or preservatives (such as sodium azide, paraformaldehyde etc.).

According to a particular embodiment, the isotonic preservation buffer optionally combined or supplemented with preservatives and/or anticoagulants is impregnated on the medium before depositing the sample of biological fluid.

According to another embodiment, the isotonic preservation buffer optionally combined or supplemented with preservatives and/or anticoagulants is impregnated concomitantly with the deposit of the sample of biological fluid.

According to a preferred embodiment, the isotonic preservation buffer optionally combined or supplemented with preservatives and/or anticoagulants is impregnated on the medium after deposit of the sample of biological fluid.

The proportions of isotonic preservation buffer and/or anticoagulant agents and/or preservatives used are those conventionally used in the field and known to those skilled in the art.

By way of example, for a sample of biological fluid according to the invention, the volume of isotonic preservation buffer and/or anticoagulant agents and/or preservatives impregnated on the medium according to the invention is between 50 and 100 μL.

By way of example, for a blood sample, the volume of isotonic preservation buffer and/or anticoagulant agents and/or preservatives impregnated on the medium according to the invention is between 10 and 50 μL.

This is advantageous because the medium according to the invention, by containing an isotonic preservation buffer with or without preservation additives and/or anticoagulants, makes it possible to preserve the sample for a longer time, which prolongs the possible storage time of the biological fluid sample while maintaining the membrane integrity of a sufficient number of cells to perform the desired analysis.

Advantageously, the sample of biological fluid is analyzed up to 168 hours after collection, preferably up to 72 hours after collection, for example 12 hours, 24 hours, 48 hours, or even 72 hours after collection.

According to a particular embodiment, the preservation of the biological sample can be reinforced by isolating the medium from the ambient air.

According to a particular embodiment, the preservation of the biological sample can be reinforced by isolating the medium from light, such as ultraviolet radiation.

Thus, in one embodiment, the device comprises at least one physical means and/or one chemical means capable of limiting the evaporation of the biological sample and/or its alteration by light.

The means capable of limiting evaporation and/or its alteration by light can, for example, be a film or equivalent impermeable to gases and liquids.

By way of example, the means capable of limiting evaporation and/or its alteration by light t can be a membrane that works as a barrier to water vapor such as a microporous membrane, or even a monolithic film such as a multilayer film.

According to a particular embodiment, in order to identify the area of collection of the medium by the patient, the medium is sandwiched between two supports, the 2 supports being perforated opposite one another to let the medium appear.

The presence of the two supports improves the rigidity of the medium. Thus, the device can be handled and easily transported. The window allows the deposit of the biological fluid sample on the medium.

According to a particular embodiment, to limit evaporation and/or protect the sample from light, one of the supports is covered with a film impermeable to gases and liquids, at least in the area facing the medium, whereas the other support is extended laterally by a flap covering at least the area of the support facing the medium, preferably the entire surface of the support.

Most biological fluids can be collected with the devices described herein, among which there may be blood or whole blood, urine, saliva, pus, serous fluid, vaginal fluid, tears, or even feces. The device is particularly suitable for blood.

According to a particular embodiment, the biological fluid is blood.

Aspects of the invention also relate to a method of collecting, preserving and storing a sample of biological fluid for cell analysis, comprising a step of depositing the sample of biological fluid on the medium of the device described above.

In practice, a sample of a biological fluid is taken which is deposited directly on the medium. The device is then preserved and/or stored and/or transported for cellular analysis of the fluid. As mentioned previously, it is not necessary that all of the cells have retained membrane integrity, the main thing being that a sufficient quantity of cells is available for analysis, possibly at least one cell, for example for a subsequent genomic analysis.

According to another characteristic, the method comprises a subsequent step of recovering the eukaryotic cells stored on the medium.

According to a particular embodiment, the recovery is accomplished by elution. It may be carried out following the collection of the sample, advantageously within 12 to 168 hours.

The eukaryotic cells thus recovered can then be analyzed. In particular, the method may comprise a subsequent step of analysis of the cells and/or of the constituents of the cells contained in the sample.

The process can be carried out with most biological fluids among which blood, urine, saliva, pus, serum, vaginal fluid, tears, or even feces. The method is particularly suitable for blood. Thus, in a particular embodiment, the sample is a blood sample.

After recovery of the sample, the preservation of the membrane integrity of the eukaryotic cells allows not only the analysis of the cells, as such, but also the analysis of most of their constituents. In particular, the constituents are chosen from:

- a. Organelles such as:
  - i. Core,
  - ii. Mitochondria,
  - iii. Lysosomes
  - iv. Exosomes
- b. Nucleic acids such as:
  - i. Messenger ribonucleic acid (mRNA),
  - ii. micro-RNA (miRNA),
  - iii. Circular deoxyribonucleic acid (DNA),
  - iv. Long non-coding RNA,
  - v. Mitochondrial DNA,
  - vi. Unfragmented DNA,
  - vii. Intact chromosomes,
- c. Proteins and Molecules such as:
  - i. Hemoglobin (HBs),
  - ii. Cytoplasmic molecules,
  - iii. Ribosomes,
- d. Intracellular parasites such as:
  - i. Plasmodium, Leishmania,
  - ii. Intracellular bacteria,
- e. and all intracellular molecules or all interesting organelles, whether endogenous or exogenous.

DESCRIPTION OF THE FIGURES

The manner of carrying out the invention, as well as the advantages which result therefrom, will emerge clearly from the description of the embodiment which follows, with the support of the appended figures.

FIG. 8 shows, in table form, the characteristics of examples of media according to the invention and counter-examples.

EXAMPLES

Example 1: Example of a Device According to an Aspect of the Invention

Figure 1:
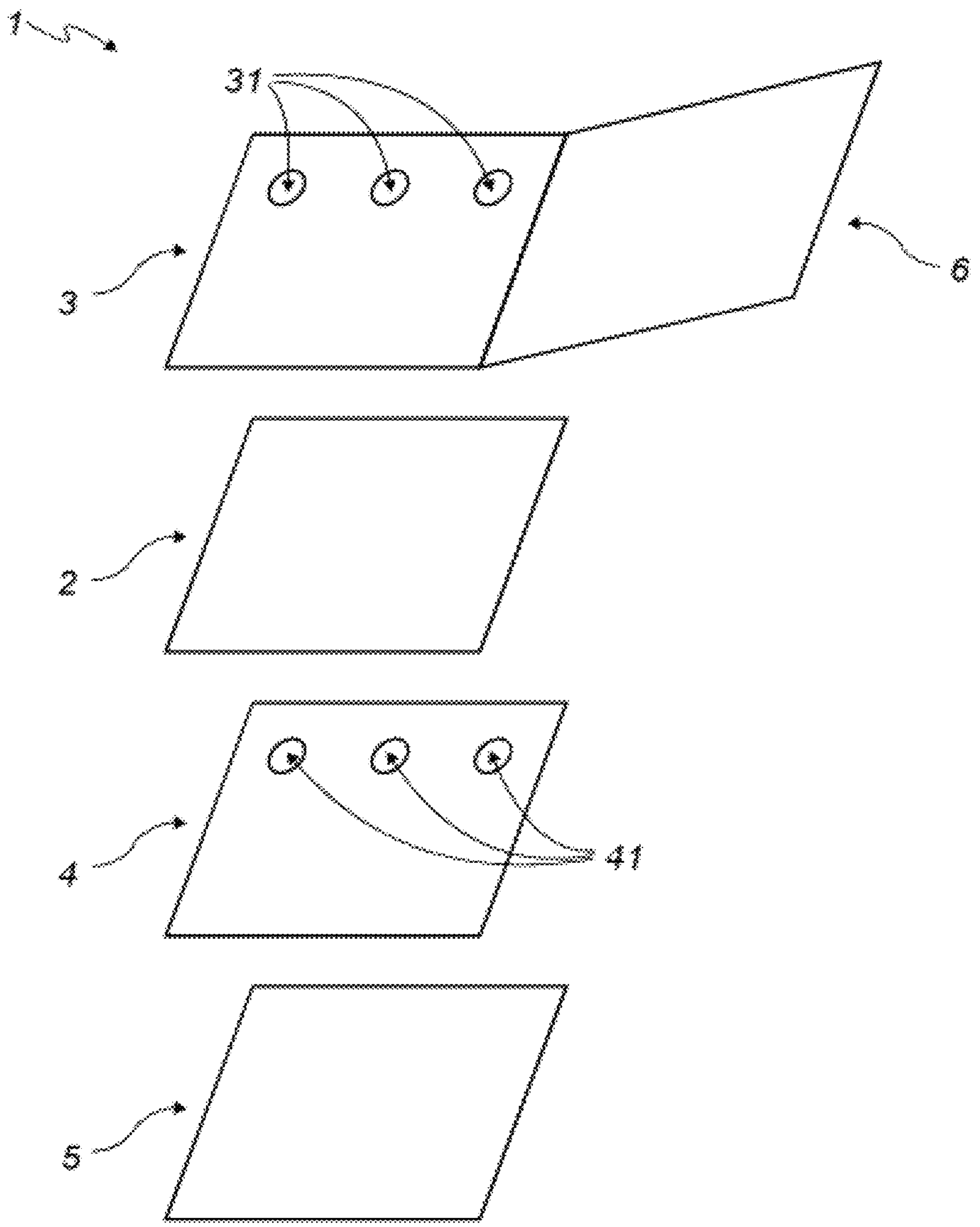
FIG. 1 shows an exploded perspective view of a collection device according to the invention.

FIG. 1 illustrates a particular embodiment of a device according to an aspect of the invention in the form of a card (1), comprising a porous medium in the form of a nonwoven (2).

The nonwoven medium (2) is sandwiched between two identical supports (3) and (4) made of cardboard. The supports (3) and (4) respectively have windows (31) and (41). These windows are placed opposite one another.

The presence of windows on the support (3) allows access to the nonwoven medium (2) for deposit of the sample of biological fluid. The presence of windows makes it possible to recover the sample deposited on the nonwoven medium (2) by punching or by creep.

An adhesive film (5) impermeable to gases and liquids is bonded to the external face of the support (4). A flap (6) is intended to be folded over the external face of the support (3) after depositing the biological sample.

The flap (6) allows, after deposit of the sample, to enclose the nonwoven medium (2) between the adhesive film (5) and the flap (6). Thus the nonwoven medium (2) and the biological sample are in a confined atmosphere isolated from air, light, and ambient humidity.

Figure 2:
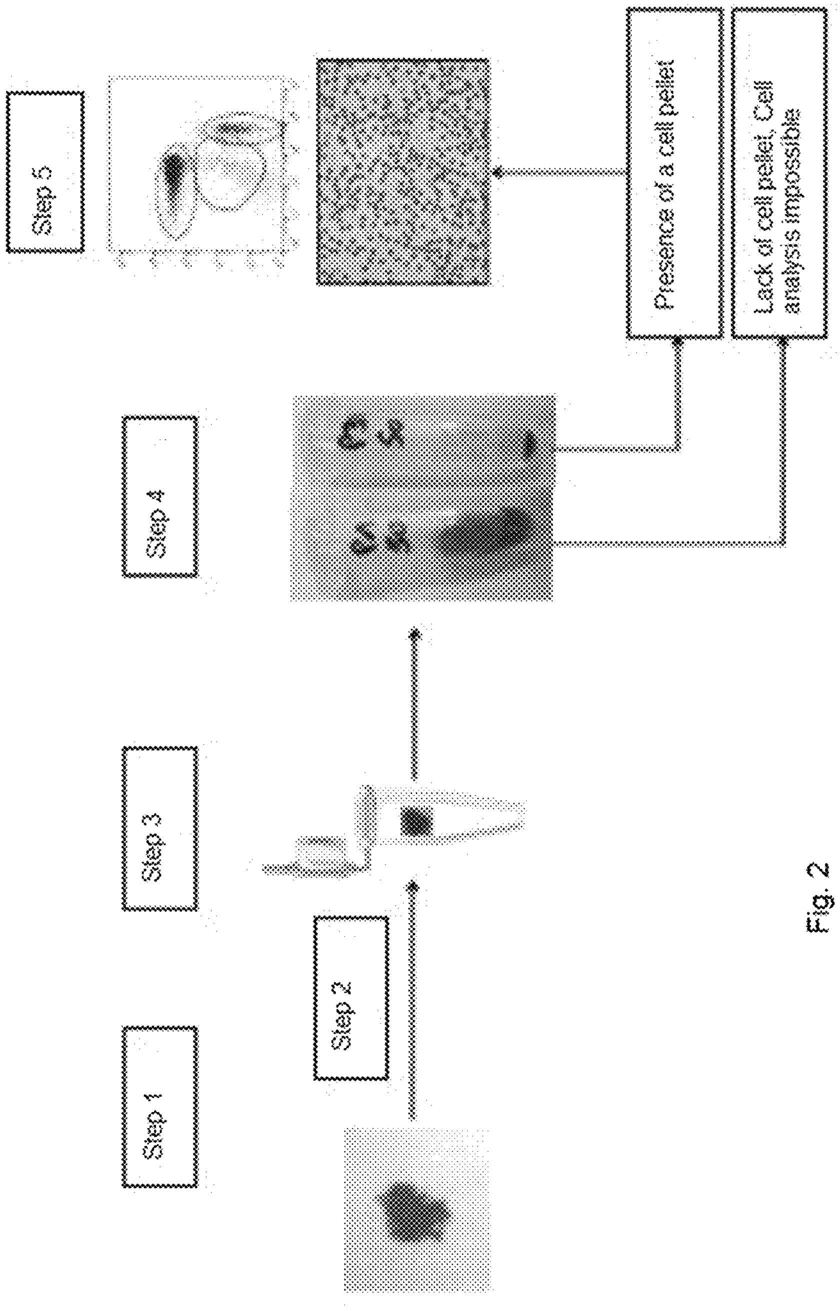
FIG. 2 represents the method of taking and collecting samples for cell analysis implementing the device according to FIG. 1.

Example 2: Implementation of the Collection Device and Cell Analysis a) Application to a Blood Sample As shown in FIG. 2, there is shown a method comprising several steps, namely:

- Step 1: Collection of the blood sample using a medium as described in Example 1, for example.
- Step 2: Storage of the device at room temperature, that is approximately 23° C.
- Step 3: Recovery of the sample by cutting out of a disc of the medium placed in a tube. Then, the cells are eluted, that is to say recovered and put in solution using an isotonic buffer, the PBS. This operation is carried out after 24 hours of storage.
- Step 4 (optional, depending on the nature of the biological sample and the type of subsequent cell analysis): Centrifugation of the eluates for 1 to 5 minutes between 300 and 600 g.

In the case where the sample does not contain intact cells, all the cell membranes are lysed, that is to say that the membrane integrity is not preserved. Centrifugation does not make it possible to obtain a cell pellet but only debris of cell constituents in suspension. In the case of a sample containing cells which have preserved their membrane integrity, the centrifugation will form a pellet consisting of the intact cells which can then be recovered for analysis. In other words and in this example, the preservation of the membrane integrity of the cells obtained from a blood sample is evaluated by centrifugation.

- Step 5: Cell analysis performed on the cell pellet obtained in step 4.

In this step, the cells recovered in Step 4 are suspended to be analyzed, for example by flow cytometry.

This technique makes it possible to sort the cell populations via the identification of fluorescence signals:

- Fluorescence emitted by the cell itself (autofluorescence);
- Fluorescence emitted by the antibody, coupled to a fluorochrome, which specifically binds to the cell.

Morphological parameters of size and granularity can also be measured and exploited by flow cytometry.

As shown in FIG. 8, the media 1 to 11, having the characteristics according to the invention, make it possible to preserve the membrane integrity of the blood cells for 24 hours after collection, on a wet (that is to say impregnated with isotonic preservation buffer) or dry medium (that is to say not impregnated with isotonic preservation buffer) and after storage at 4° C. or at room temperature (23-25° C.).

In addition, when the media 1 to 11 are impregnated with an isotonic preservation buffer, the preservation of the membrane integrity of the cells of the sample extends up to 72 hours after their collection and storage at 4° C. or at room temperature (23-25° C.).

The medium 12 makes it possible to preserve the membrane integrity of the cells of the sample after 24 hours of storage at 4° C. or at room temperature in a humid environment, and after 24 hours of storage at 4° C. in a dry environment.

The media 13 and 14 (counter-examples) do not have the characteristics according to the invention (these media contain 100% natural fibers, by weight). The results show that these media when used in dry conditions, that is to say without impregnation with an isotonic preservation buffer, do not allow the membrane integrity of the cells to be preserved after 24 hours of storage at 4° C. or at room temperature (23-25° C.).

The media 15 and 16 (counter-examples) do not have the characteristics according to the invention. In particular, these media have an MFP of less than 3 μm (respectively 2.2 μm and 2.9 μm), not allowing the membrane integrity of the cells of a blood sample to be preserved, whatever the collection, preservation and storage conditions. Accordingly, the MFP is a key parameter in order to preserve the membrane integrity of the cells.

The determination of the survival of the cells of the blood sample was evaluated after 72 hours of storage in a dry medium, at 4° C. or at room temperature.

The results are shown in Table 1.

TABLE 1

| | Composition (in % by total weight of the medium) | Thickness (μm) at 100 Kpa | MFP (μm) | 72 hours DRY ENVIRONMENT 4° C. | 72 hours DRY ENVIRONMENT Room temperature |
|---|---|---|---|---|---|
| Medium No. 1 | 100% PET | 110 | 70 | Yes | Yes |
| Medium No. 2 | 91% of glass fiber + 9% PVOH | 324 | 119 | Yes | Yes |

The results of Table 1 show that the membrane integrity is preserved, at least for media 1 and 2, after 72 hours of storage at 4° C. or at room temperature, in a dry medium, that is to say without adding isotonic conservation buffer.

b) Analysis of Results

The cell pellet obtained at the end of step 4 mentioned above contains in particular red blood cells (erythrocytes) and white blood cells (leukocytes).

Red cells are anucleate eukaryotic cells, that is to say cells devoid of a nucleus following its expulsion during the differentiation of the erythrocyte lineage, as mentioned previously. They have a characteristic concave shape which allows their identification via phase contrast microscopy.

Figure 3:
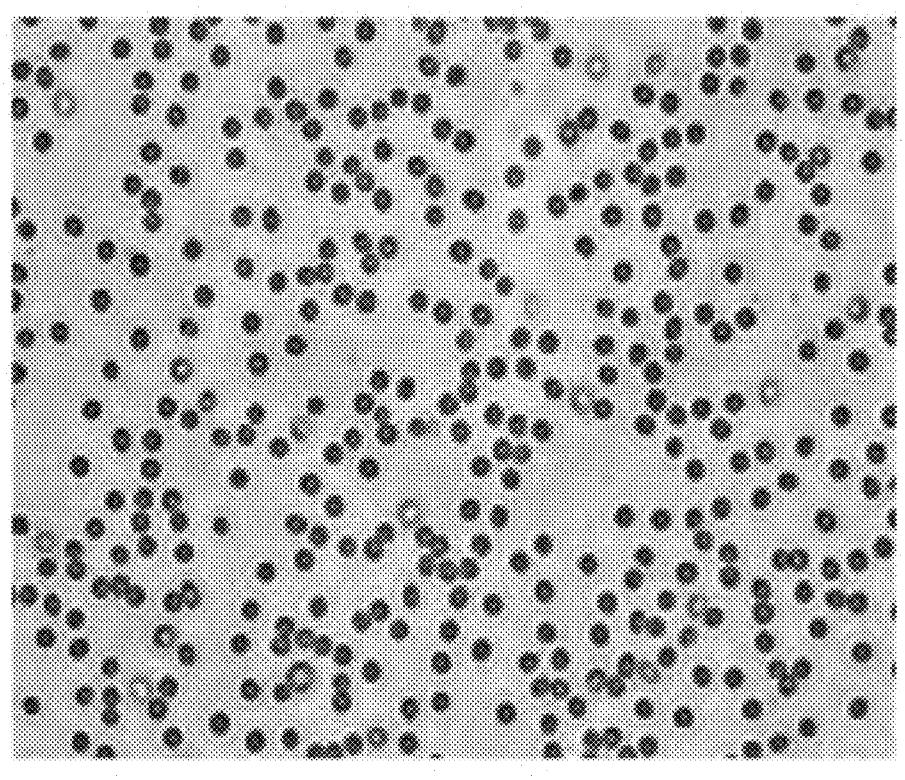
FIG. 3 is a photograph by phase contrast microscopy of the sample obtained by means of the device according to FIG. 1 implemented in the method of FIG. 2.

Leukocytes have a nucleus, possibly multilobed. The presence of this nucleus then induces a change in phase of the light wave which makes it possible to identify them. The results are shown in FIG. 3.

The dark cells correspond to red blood cells and the white cells to leukocytes. This photograph confirms that the cells have retained their membrane integrity, all the way to their shape, as shown by the biconcavity that is characteristic of red blood cells, thus making it possible to analyze them.

These visual results are confirmed by an analysis of the sample by flow cytometry, either by autofluorescence or by binding to particular antibodies (anti-CD8, anti-EpCAM, etc.).

This type of identification requires the use of specific markers expressed on the surface of the cells, which implies that the membrane integrity is preserved.

The results obtained after analysis of the sample by flow cytometry are presented in the form of a 2-dimensional diagram.

Figure 4:
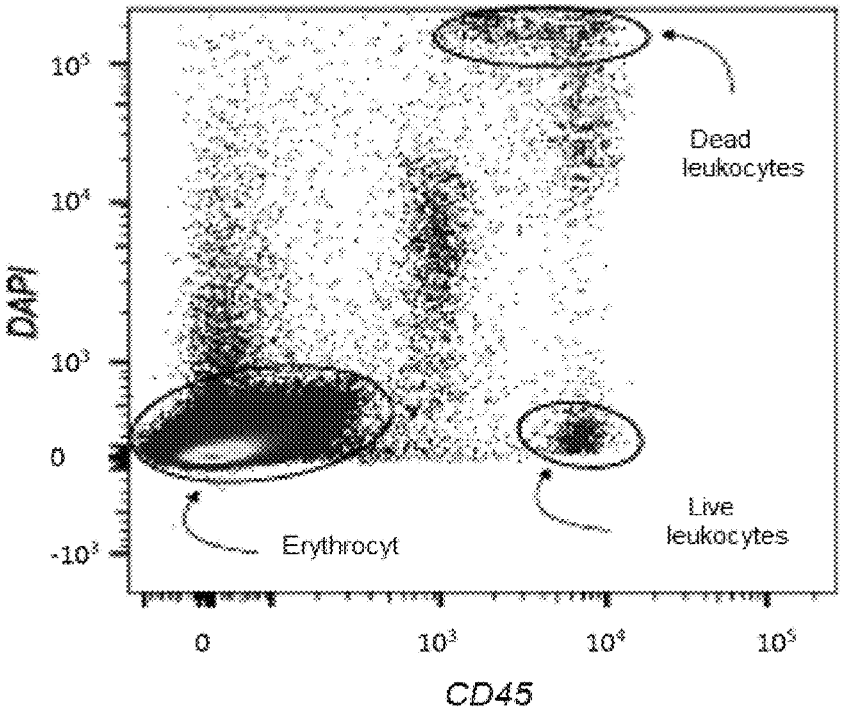
FIG. 4 represents a two-dimensional diagram obtained after an analysis by flow cytometry, on the basis of the expression of the specific DAPI and CD45 markers, of a biological sample obtained by means of the device of the FIG. 1 implemented in the method of FIG. 2.

As shown in FIG. 4, the identification and the analysis or the cell sorting are carried out on the basis of the expression of the specific DAPI (4',6-diamidino-2-phenylindole) and CD45 ("cluster of differentiation 45" or differentiation group) markers present on the surface of cells.

Thus, the cells emitting a weak fluorescence corresponding to the DAPI signal as well as a weak fluorescence corresponding to the CD45 signal ($DAPI^-$ and $CD45^-$) are anucleate cells (no DAPI labeling), which are not leukocytes (no CD45 marking). These cells are identified as corresponding to red blood cells.

Similarly, the $DAPI^-$ and $CD45^+$ cells are living leukocytes and the $DAPI^+$ and $CD45^+$ cells are dead leukocytes but which have kept their membrane integrity.

Figure 5:
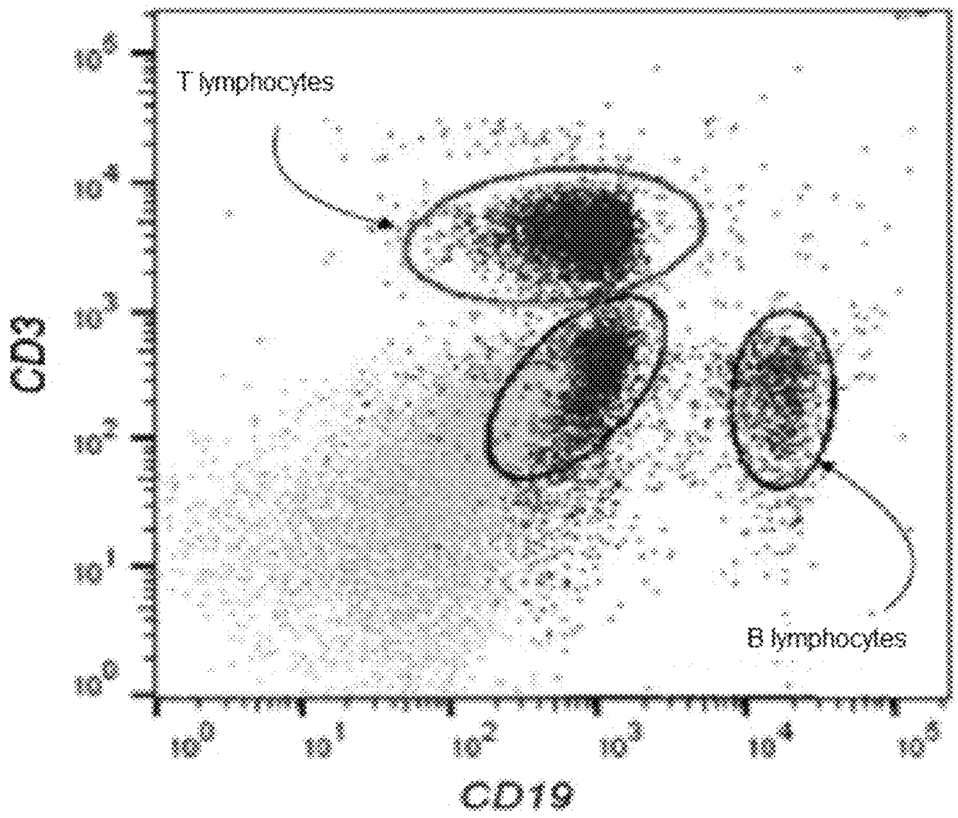
FIG. 5 represents a two-dimensional diagram obtained after an analysis by flow cytometry, on the basis of the expression of the specific markers CD3 and CD19, of a cell population.

After the identification and collection of these different cell types and using multiplexing, the previously identified living leukocytes are analyzed to identify the subpopulations (FIG. 5):

$CD3^-$ and $CD19^+$: B lymphocytes; and $CD3^+$ and $CD19^-$: T lymphocytes.

Figure 6:
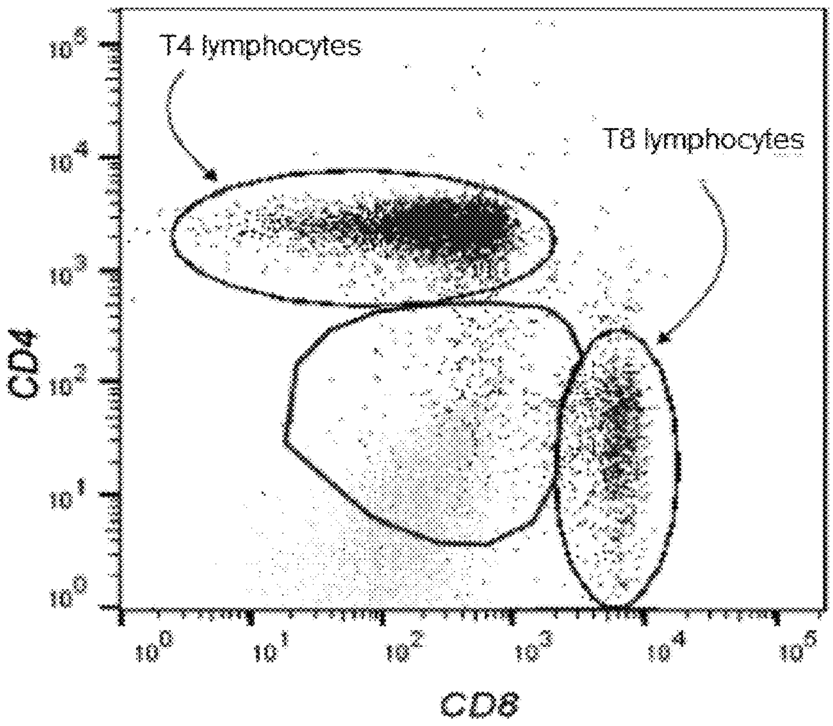
FIG. 6 represents a two-dimensional diagram obtained after an analysis by flow cytometry, on the basis of the expression of the specific CD4 and CD8 markers, of a cell population.

After the identification and collection of these different cell types, the T lymphocytes are analyzed to identify the subpopulations (FIG. 6):

$CD4^-$ and $CD8^+$: T8 lymphocytes; and $CD4^+$ and $CD8^-$: T4 lymphocytes.

Figure 7:
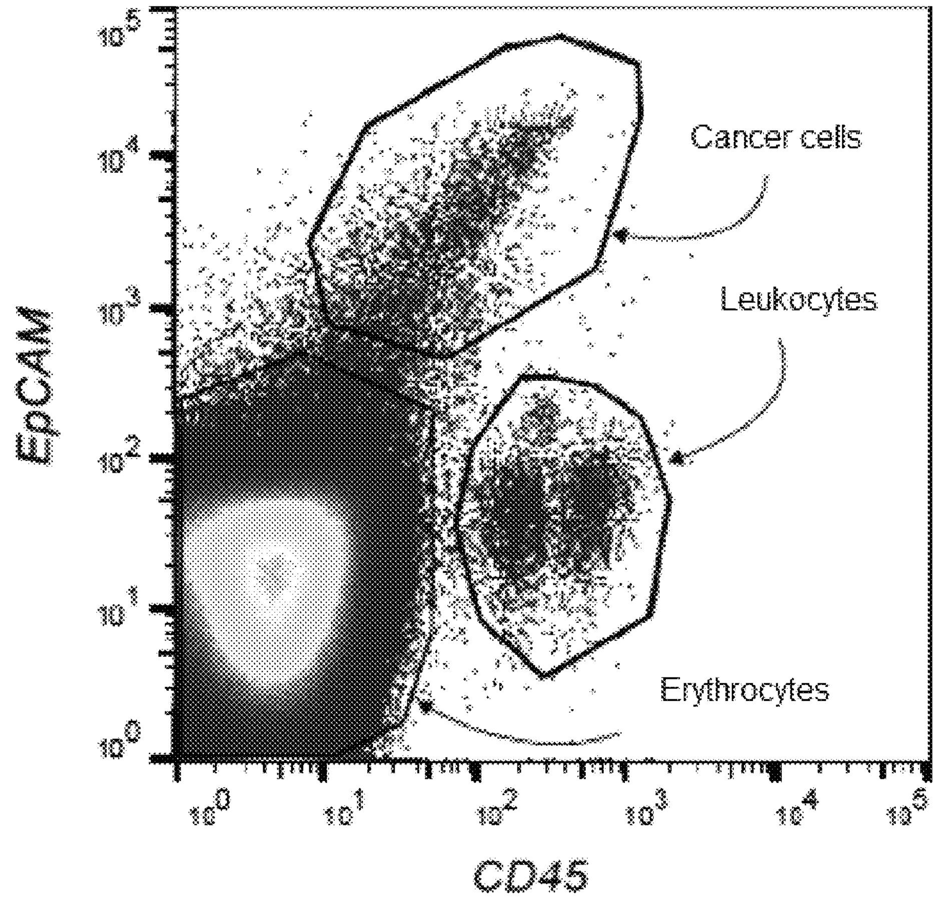
FIG. 7 represents a two-dimensional diagram obtained after an analysis by flow cytometry, on the basis of the expression of the specific EpCAM and CD45 markers, of a cell population.

The different cell populations present in a sample obtained using the device according to the invention can be identified by flow cytometry. FIG. 7 represents the identification of red blood cells, leukocytes and cancer cells depending on whether the cells express the EpCAM ("Epithelial cell adhesion molecule") and CD45 biomarkers, in a blood sample obtained by means of the device according to the invention.

Thus, the populations present in the sample are:

$EpCAM^-$ and $CD45^-$: red blood cells;

$EpCAM^-$ and $CD45^-$: leukocytes; and $EpCAM^+$: cancer cells.

As these results show, the device of the invention makes it possible to collect, preserve and store, thanks to the media which it contains, a sample of biological fluid under conditions such that the membrane integrity of the cells is preserved, thus making further cell analysis possible.

The invention claimed is:

1. A device for collecting, preserving and storing a sample of biological fluid, wherein the device comprises a porous nonwoven medium for collecting and maintaining the membrane integrity of the eukaryotic cells contained in the sample, and their constituents, the medium comprising at least 80% by weight of artificial components of a total weight of the medium, wherein the artificial components comprise semisynthetic fibers and/or synthetic fibers; wherein the medium has a mean flow pore size (MFP) of between 3 μm and 200 μm and a thickness between 100 μm and 2500 μm, and wherein the medium is sandwiched between two supports, the two supports being perforated opposite one another to allow the medium to appear.

2. The device according to claim 1, wherein the artificial component comprises:

semisynthetic fibers chosen from the group comprising: rayon fibers, lyocell fibers, viscose fibers, and mixtures thereof; and/or synthetic fibers chosen from the group comprising: polyethylene terephthalate (PET) fibers, glass fibers, glass microfibers, and their mixtures.

3. The device according to claim 1, wherein the medium comprises up to 15% by weight of a binder.

4. The device according to claim 1, wherein the medium has an MFP of between 10 μm and 200 μm.

5. The device according to claim 1, wherein the semi-synthetic fibers and/or the synthetic fibers have a moisture regain value of less than 5%, measured by the ASTM D269-15 (2015) standard.

6. The device according to claim 1, wherein the semi-synthetic fibers and/or the synthetic fibers have a contact angle with water of less than 75°.

7. The device according to claim 1, wherein the medium contains exclusively semi-synthetic fibers and/or synthetic fibers.

8. The device according to claim 1, wherein the medium is impregnated with an isotonic preservative and optionally at least one preservative and/or at least one anticoagulant agent.

9. The device according to claim 1, wherein the device further comprises at least one physical and/or chemical means capable of limiting the evaporation of the biological sample.

10. The device according to claim 1, wherein the medium has a thickness between 200 μm and 1200 μm.

11. The device according to claim 1, wherein one of the supports is covered with a film impermeable to gases and liquids, at least in the region opposite the medium, while the other support is extended laterally by a flap covering at least the area of the support facing the medium.

12. The device according to claim 1, wherein the device is in the form of a card.

13. The device according to claim 1, wherein each support of the two supports comprises a plurality of windows.

14. A method for collecting, preserving and storing a sample of biological fluid for cell analysis, comprising a step of depositing a sample of said biological fluid on the medium of the device according to claim 1.

15. The method according to claim 14, wherein the method further comprises a step of impregnating the medium with an isotonic preservation buffer and optionally at least one preservative and/or at least one anticoagulant agent.

16. The method according to claim 14, wherein the method further comprises a subsequent step of recovering the cells stored on the medium by elution.

17. The method according to claim 14, wherein the sample is a blood sample.

18. The method according to claim 14, wherein the constituents are chosen from:

a. Organelles selected from:
  i. Core,
  ii. Mitochondria,
  iii. Lysosomes, or
  iv. Exosomes, b. Nucleic acids selected from:
  i. Messenger ribonucleic acid (mRNA),
  ii. micro-RNA (miRNA),
  iii. Circular deoxyribonucleic acid (DNA),
  iv. Long non-coding RNA,
  v. Mitochondrial DNA,
  vi. Unfragmented DNA, or
  vii. Intact chromosomes, c. Proteins and Molecules selected from:
  i. Hemoglobins (HBs),
  ii. Cytoplasmic molecules, or
  iii. Ribosomes, d. Intracellular parasites selected from:
  i. *Plasmodium, Leishmania,*
  ii. Intracellular bacteria, or e. all intracellular molecules or all organelles, whether endogenous or exogenous.

* * * * *